United States Patent [19]

Tóth et al.

[11] Patent Number: 5,118,693
[45] Date of Patent: Jun. 2, 1992

[54] 4,4-DISUBSTITUTED PIPERIDINE DERIVATIVES, PHARMACEUTICAL COMPOSITIONS CONTAINING THEM AND PROCESS FOR PREPARING SAME

[75] Inventors: Edit Tóth; József Törley; Sándor Görög; László Szporny; Béla Kiss; Éva Pálosi; Dóra Groó; István Laszlovszky; Erzsébet Lapis; Ferenc Auth; László Gaál, all of Budapest, Hungary

[73] Assignee: Richter Gedeon Vegyeszeti Gyar Rt., Budapest, Hungary

[21] Appl. No.: 566,273

[22] Filed: Aug. 10, 1990

[30] Foreign Application Priority Data

Aug. 10, 1989 [HU] Hungary .............. 4094/89
May 29, 1990 [HU] Hungary .............. 3233/90

[51] Int. Cl.⁵ .................. A61K 31/445; C07D 211/40
[52] U.S. Cl. .................. 514/327; 546/221; 546/222
[58] Field of Search .................. 546/222, 226, 228; 514/345, 346, 327

[56] References Cited

U.S. PATENT DOCUMENTS 2,838,518 6/1958 Schuler .................. 546/222

OTHER PUBLICATIONS

Jones et al., "Substituted 1,1-Diphenyl . . ." J. Med. Chem. 14(2) 161–164 (1971).
Chem. Abstracts 52:451g (1958).
Chem. Abstracts 53:20054c (1959).
Chem. Abstracts 53:20206e (1959).
Chem. Abstracts 56:447a–e (1962).
Chem. Abstracts 59:7473e–h (1963).
Chem. Abstracts 69:86169w (1968).
Chem. Abstracts 69:100226w (1968).
Chem. Abstracts 72:43382e (1970).
Chem. Abstracts 73:87739b (1970).
Chem. Abstracts 78:23876q (1973).
Chem. Abstracts 81:33153c (1974).
Chem. Abstracts 91:203709x (1981).
Chem. Abstracts 100:6570r (1984).
Chem. Abstracts 100:6627q (1984).
Chem. Abstracts 100:209608g (1984).
Chem. Abstracts 103:160352q (1985).
Chem. Abstracts 104:88618g (1986).
Chem. Abstracts 109:190261a (1988).
Methoden der Org. Chem., vol. VIII, pp. 106–107 (1952).
Berichte, 55, p. 3413 (1922).
J. Chem. Soc., pp. 4071–4072 (1959).
Coll. Czech Chem Comm., vol. 38, pp. 3879–3901 (1973).
Protection for the Amino Group, pp. 218–287.

Primary Examiner—C. Warren Ivy
Assistant Examiner—Celia Chang
Attorney, Agent, or Firm—Herbert Dubno; Andrew Wilford; Jonathan Myers

[57] ABSTRACT

The invention relates to novel, therapeutically active 4,4-disubstituted piperidine derivatives of the formula (I),

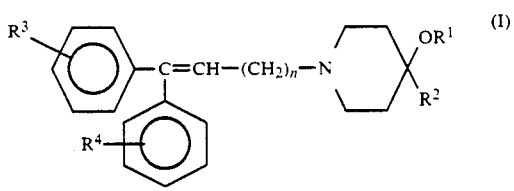

wherein
$R^1$ means hydrogen or —CONHR group, wherein
  R stands for hydrogen, $C_{1-12}$alkyl, $C_{3-6}$cycloalkyl, carbocyclic $C_{6-10}$aryl or carbocyclic $C_{6-10}$aryl-$C_{1-4}$alkyl group, the latter two being optionally substituted on their aromatic moiety by one or more, same or different halogen(s) or one of more $C_{1-4}$alkyl or $C_{1-4}$alkoxy group(s);
$R^2$ stands for an ethynyl or acetyl group;
$R^3$ and $R^4$, which are the same or different, represent hydrogen, one or more halogen(s), $C_{1-4}$alkyl, $C_{1-4}$alkoxy, trihalomethyl group or hydroxyl group optionally esterified by a $C_{1-4}$alkanoic acid; and
n is 1 or 2, as well as their pharmaceutically acceptable acid addition and quaternary ammonium salts.

7 Claims, No Drawings

4,4-DISUBSTITUTED PIPERIDINE DERIVATIVES, PHARMACEUTICAL COMPOSITIONS CONTAINING THEM AND PROCESS FOR PREPARING SAME

The invention relates to novel, therapeutically active 4,4-disubstituted piperidine derivatives of the formula (I),

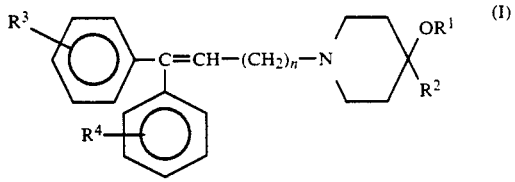

wherein
- $R^1$ means hydrogen or —CONHR group, wherein R stands for hydrogen, $C_{1-12}$alkyl, $C_{3-6}$cycloalkyl, carbocyclic $C_{6-10}$aryl or carbocyclic $C_{6-10}$aryl-$C_{1-4}$alkyl group, the latter two being optionally substituted on their aromatic moiety by one or more, same or different halogen(s) or one or more $C_{1-4}$alkyl or $C_{1-4}$alkoxy group(s);
- $R^2$ stands for an ethynyl or acetyl group;
- $R^3$ and $R^4$, which are the same or different, represent hydrogen, one or more halogen(s), $C_{1-4}$alkyl, $C_{1-4}$alkoxy, trihalomethyl group or hydroxyl group optionally esterified by a $C_{1-4}$alkanoic acid; and
- n is 1 or 2, as well as their pharmaceutically acceptable acid addition and quaternary ammonium salts and pharmaceutical compositions containing these compounds.

The invention also relates to a process for the preparation of the above compounds and compositions as well as to a method of treatment. The latter comprises administering a therapeutically effective amount of a compound of the formula (I) or a pharmaceutically acceptable acid addition or quaternary ammonium salt thereof alone or in the form of a pharmaceutical composition to a patient for treating psychotic disorders.

The compounds of the formula (I) may exist in various stereoisomeric forms such as geometrical and optical isomers, racemates, separated optical isomers and their mixtures, all of which may occur in the form of various solvates and hydrates. All these compounds and mixtures are within the scope of the invention.

4,4-Disubstituted piperidine derivatives have been described e.g. in the following publications: C.A. 52, 451g, 20206e (1958); C.A. 53, 20054c (1959); C.A. 56, 447c, (1962); C.A. 59, 7473h (1963); C.A. 69 86169w, 100226w (1968); C.A. 72, 43382e; C.A. 73, 87739b (1970); C.A. 78 23876q (1973); C.A. 81, 33153c (1974); C.A. 95, 203709x (1981); C.A. 10, 6227q, 209608g (1984); C.A. 103, 160352q (1985); as well as in the U.S. Pat. Nos. 4,405,631 and 4,521,537 and in the EP patent specification No. 275,962.

A substantial difference between the compounds of formula (I) according to the invention and similar derivatives known up to the present appears in the nature of the substituents bound in position 1 of the piperidine moiety.

According to an other aspect of the invention, there is provided a process for the preparation of compounds of the formula (I) as well as their acid addition or quaternary ammonium salts, which comprises a) ethynylating a 4-piperidone compound of the formula (II),

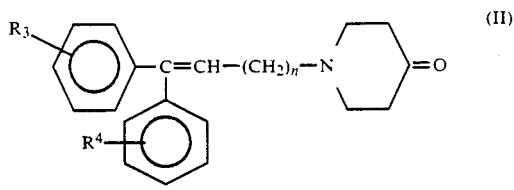

wherein $R^3$ and $R^4$ are as defined above, to obtain compounds of the formula (I), wherein $R^1$ is hydrogen, $R^2$ is an ethynyl group and $R^3$, $R^4$ as well as n are as defined above; or b) hydrolytically cleaving a 2-oxo-1,3-dioxa-8-azaspiro[4,5]decane derivative of the formula (III),

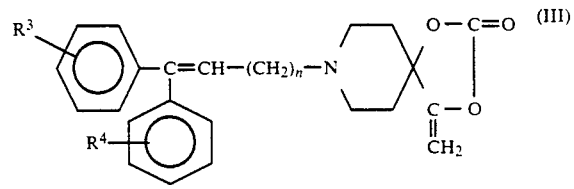

wherein $R^3$, $R^4$ and n are as defined above, to obtain compounds of the formula (I), wherein $R^1$ is hydrogen, $R^2$ is an acetyl group and $R^3$, $R^4$ as well as n are as defined above; or c) reacting a piperidine derivative of the formula (IV),

wherein $R^1$ and $R^2$ are as defined above, with a diphenylalkene derivative of the formula (V),

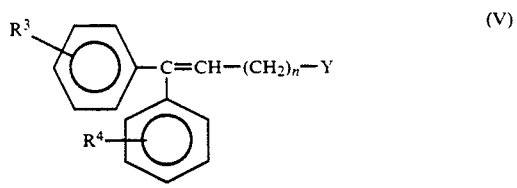

wherein $R^3$, $R^4$ and n are as defined above and Y means halogen, $C_{1-4}$alkylsulfonyloxy or arylsulfonyloxy group; or d) reacting a carbonate ester derivative of the formula (VI),

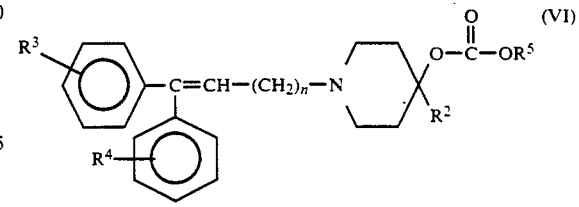

wherein $R^2$, $R^3$, $R^4$ and n are as defined above and $R^5$ means a phenyl group optionally substituted by one or more halogen(s) or nitro group, with an amine of the formula $R-NH_2$, where R is as defined above, to prepare compounds of the formula (I), wherein $R^1$ stands for a —CONHR group and R, $R^2$, $R^3$, $R^4$ and n are as defined above; then, if desired, transforming a functional group of a thus-obtained compound of the formula (I), whrein $R^1$, $R^2$, $R^3$, $R^4$ and n are as defined above, to an other one in a known manner; and/or hydrating a thus-obtained piperidine derivative of the formula (I), wherein $R^2$ means an ethynyl group and $R^1$, $R^3$, $R^4$ as well as n are as defined above, to obtain compounds of the formula (I), wherein $R^2$ stands for an acetyl group and $R^1$, $R^3$, $R^4$ as well as n are the same as defined above; and/or reacting a thus-obtained compound of the formula (I), wherein wherein $R^1$ means hydrogen and $R^2$, $R^3$, $R^4$ as well as n are as defined above, with a suitably substituted reactive carbamic acid derivative to obtain compounds of the formula (I), wherein $R^1$ represents a —CONHR group, $R^2$, $R^3$, $R^4$ as well as n are as defined above and R is as defined above, except hydrogen; and/or reacting a thus-obtained compound of the formula (I), wherein $R^1$, $R^2$, $R^3$, $R^4$ and n are as defined above, with an acid to give an acid addition salt and/or treating a compound of the formula (I), wherein $R^1$, $R^2$, $R^3$, $R^4$ and n are as defined above, obtained as a salt with a base to liberate the free basic form thereof and/or converting a thus-obtained compound of the formula (I), wherein $R^1$, $R^2$, $R^3$, $R^4$ and n are as defined above, to its quaternary ammonium salt.

In the process a) according to the invention a 4-piperidone derivative of the formula (II) is made to react with an alkaline metal acetylide. This ethynylating reaction is carried out by using the acetylide of lithium, sodium or potassium. For the formation of the alkaline metal acetylide e.g. alkaline metals or hydroxides, amides or alkoxides of alkaline metals may be employed. This reaction is performed in a solvent medium. Suitable solvents are e.g. liquid ammonia; aliphatic and alicyclic ethers such as diethyl ether, dipropyl ether, 1,2-dimethoxyethane, tetrahydrofuran, dioxane; aliphatic alcohols such as isobutyl alcohol, tertiary butanol; acid amides such as N,N-dimethylformamide, N-methylacetamide, N-methylpyrrolidone; aliphatic, alicyclic or aromatic hydrocarbons such as hexane, cyclohexane, benzene, toluene or xylene; sulfoxides such as dimethyl sulfoxide; or mixtures of the above solvents. The ethynylation can be carried out under atmospheric or a higher pressure. This reaction is preferably carried out in such a way that the 4-piperidone derivative of the formula (II) is brought into reaction with acetylene under atmospheric pressure, in the presence of an alkaline metal tertiary alkoxide and an organic solvent.

In the process b) according to the invention a spirodecane derivative is hydrolytically cleaved. This reaction is preferably realized under basic conditions, in a solvent medium containing water. Suitable bases are e.g. carbonates and hydroxides of alkaline metals and/or tertiary organic bases. This reaction may be carried out in a wide temperature range, e.g. at a temperature between 0° C. and the boiling point of the reaction mixture, preferably between 20° C. and 140° C., under an inert gas such as argon or nitrogen.

In the process c) according to the invention a piperidine derivative of the formula (IV) is reacted with a diphenylalkene derivative of the formula (V). In the latter formula Y means e.g. a mesyloxy (methanesulfonyloxy) or tosyloxy (toluenesulfonyloxy) group or halogen, preferably chlorine or bromine. This reaction is preferably accomplished in an inert organic solvent in the presence of a base being capable of binding the acid liberated in the reaction. Suitable solvents are e.g. aliphatic alkanols such as ethanol, isopropanol or butanol; aromatic hydrocarbons such as chlorobenzene or toluene; ethers such as dibutyl ether or dioxane; tertiary aliphatic acid amides such as dimethylformamide, dimethylacetamide; ketones such as acetone, methyl ethyl ketone or methyl isobutyl ketone; but a mixture of the above solvents may be employed, too. For binding the acid liberated in the reaction, inorganic or tertiary organic bases, e.g. carbonates or hydrogen carbonates of alkaline metals or alkaline earth metals as well as organic bases, e.g. triethylamine, dimethylaniline or pyridine may be used; though an excess of the compound of the formula (IV) is also suitable for this purpose. This reaction may be carried out between room temperature and the boiling point of the reaction mixture; optionally, a catalyst may also be added. Suitable catalysts are alkaline metal iodides. It is preferably to work under an inert gas such as nitrogen or argon.

In the process d) according to the invention a carbonate ester of the formula (VI) is brought into reaction with an amine of the formula $R-NH_2$. This reaction may be performed in the presence of or without any solvent. Suitable solvents are e.g. aliphatic, alicyclic or aromatic hydrocarbons such as hexane, cyclohexane, benzene, chlorobenzene, nitrobenzene or xylene; ethers such as diethyl ether, di-n-butyl ether, tetrahydrofuran and dioxane; alcohols such as ethanol, butanol, cyclohexanol or benzyl alcohol; tertiary organic bases such as picoline, pyridine or triethylamine; or an excess of the $R-NH_2$ amine may also be utilized as solvent. Any mixture of the above solvents may also be employed. The reaction is carried out between $-35°$ C. and the boiling point of the reaction mixture. It is advantageous to use an inert gas environment such as argon or nitrogen in this reaction.

If desired, the compounds of the formula (I) obtained by using the processes a) to d) can be transformed to other compounds being within the scope of the formula (I) in a manner known per se.

Thus, by hydrating a compound of the formula (I) containing an ethynyl group as $R^2$, compounds of the formula (I) are obtained, wherein $R^2$ means an acetyl group.

In the course of this transformation a 4-ethynyl-4-piperidinol derivative of the formula (I) is reacted with water in the presence of a mercuric compound, optionally in an acidic medium, suitable mercuric compounds for this purpose are e.g. mercuric oxide, mercuric chloride, mercuric sulfate, mercuric acetate, mercuric acetamide or mercuric p-toluenesulfonamide. Sulfuric or acetic acid may e.g. be used as acids. Suitable solvents are e.g. aliphatic alcohols such as methanol or ethanol; aliphatic ketones such as acetone; aliphatic carboxylic acid esters such as ethyl acetate; alicyclic ethers such as dioxane and tetrahydrofuran; or mixtures of the above solvents. This reaction is carried out in a temperature range between room temperature and the boiling point of the reaction mixture. Optionally, mercury can be removed by using hydrogen sulfide.

If desired, compounds of the formula (I) containing —CONHR group as $R^1$ can be prepared by reacting a 4-piperidinol derivative of the formula (I) with an appropriately substituted reactive carbamic acid derivative. As a reactive carbamic acid derivative e.g. a carbamic acid halide of the formula (VII).

R—NHCOX (VII)

wherein R is as defined above, except hydrogen, and X means halogen, or an isocyanate of the formula R—NOC, wherein R is as defined for formula (VII), may be used. This reaction is realized in an organic solvent, which is inert under the reaction conditions, in the presence of a suitable inorganic and/or tertiary organic base. Suitable solvents are e.g. aliphatic or alicyclic ethers such as diethyl ether, di-propyl ether, diisopropyl ether, dioxane or tetrahydrofuran; aliphatic, alicyclic or aromatic hydrocarbons such as methylene chloride, hexane, cyclohexane, benzene, toluene or xylene; nitriles such as acetonitrile; acid amides such as dimethylformamide or N-methylpyrrolidone; sulfoxides such as dimethyl sulfoxide; or mixtures of the above solvents. An excess of the tertiary organic base, e.g. and excess of pyridine or triethylamine may also be employed. Finally, the reaction may also be carried out without any solvent, e.g. in a molten state.

The reaction is highly accelerated by inorganic or tertiary organic bases; therefore, it is suitable to carry out this reaction in the presence of such bases. As basic catalysts e.g. amides, carbonates or hydroxides of alkaline metals and/or tertiary organic bases, e.g. pyridine, triethylamine, 4-dimethylaminopyridine, triethylenediamine and the like may be employed.

The temperature of the reaction may be varied under wide limits: usually, the reaction is performed in a temperature range between 5° C. and the boiling point of the reaction mixture, preferably between 10° C. and 140° C. It is preferably to use an inert gas atmosphere, e.g. nitrogen or argon.

If desired, the compounds of the formula (I) can be transformed to their acid addition or quaternary ammonium salts by using methods known per se. For the preparation of acid addition salts inorganic or organic acids such as hydrogen halides, e.g. hydrochloric acid and hydrobromic acid; sulfuric acid, phosphoric acids as well as formic, acetic, propionic, oxalic, glycolic, maleic, fumaric, succinic, tartaric, ascorbic, citric, malic, salicylic, lactic, benzoic, cinnamic, aspartic, glutamic, N-acetyl-aspartic or N-acetylglutamic acid as well as alkanesulfonic acids such as methanesulfonic acid or arenesulfonic acids, e.g. p-toluene-sulfonic acid and the like, may be used.

The salt formation can be carried out e.g. in such a way that the corresponding acid is added t the solution of the compound of the formula (I) prepared in an inert solvent, e.g. ethanol, and the salt formed is precipitated by adding preferably a water-immiscible organic solvent, e.g. diethyl ether.

For the preparation of quaternary ammonium salts a lower alkyl, alkenyl or benzyl halide or an alkyl sulfate may favorably be employed. The quaternization is suitably performed in an organic solvent such as acetone, acetonitrile, ethanol or their mixtures at a temperature range from room temperature up to the boiling point of the solvent.

The acid addition or quaternary ammonium salt obtained may be isolated e.g. by filtration and, when necessary, purified by recrystallization.

Conversely, the corresponding free bases can be liberated from their salts by an alkaline treatment.

The starting substances used n the process of the invention are partly known or can be prepared by using known methods.

The compounds of the formulae (II) and (V) can be prepared e.g. according to the following literature references: Ber. 55, 3406 (1922); Ann. Chem. 555, 80 (1952); GB patent specification No. 683,950; Yakugaku Zasshi 82, 1088 (1952); J. Chem. Soc. 4066 (1959); Coll. Czechoslov. Chem. Commun. 38, 3879 (1973).

The preparation of the compounds of the formula (III) is described in the Hungarian patent application No. 4094/89 filed on Aug. 10, 1989 and in the concurrently filed copending commonly assigned U.S. applications Ser. No. 07/556,278 and Ser. No. 07/556,279.

The compounds of the formula (IV) are obtained e.g. by removing the N-protective group of suitably substituted piperidine derivatives by using methods commonly known from the literature [see e.g. T. W. Green: "Protective Groups in Organic Synthesis", Ed. John Wiley, New York, pages 218 to 288 (1981)].

The carbonate esters of the formula (VI) can be prepared e.g. by reacting suitably substituted 4-hydroxypiperidine derivatives with the corresponding chloroformates [see e.g. Houben-Weyl: Methoden der Organischen Chemie, Vol. VIII page 106 (1952)].

The new compounds of the formula (I) according to the invention are, on the one hand, valuable intermediates in the synthesis of compounds exerting antipsychotic and cognitive function-improving effects (see the Hungarian patent applications Nos. 4094/89 and 4095/89 and, on the other hand, they exert their own preferably biological activity e.g. on the central nervous system, too. This central nervous system action of the compounds of the present invention was investigated by using the methods described hereinafter.

1) Inhibition of the tetrabenazine-induced catalepsy

Male Hannover-Wistar rats weighing 160 to 180 g each were used in these examinations. Various doses of the test compounds were orally administered in an aqueous suspension containing 10% of Tween 80. After oral doses of the test substances the groups consisting of 5 animals each were intraperitoneally (i.p.) treated with a 30 mg/kg dose of tetrabenazine (9,10-dimethoxy-3-isobutyl-2-oxo-1,2,3,4,6,7-hexahydro-11b(H)-benzo[a]-quinolizine). The control group was treated with a placebo, i.e. the suspension containing no test compound. The behavior of the animals was hourly observed for 3 hours. An animal was considered to be cataleptic when it did not correct within 30 seconds its whimsical body position caused by lifting its upper limbs onto a 7 cm high column.

2) Inhibition of the pentylenetetrazole-induced seizure

Groups consisting of 10 male CFLP/LATI mice weighing 18–22 g each were used in these examinations. Various doses of the test compounds were orally administered to the animals in an aqueous suspension containing 10% of Tween 80. One hour after this pretreatment, the animals were subcutaneously treated with a dose of 125 mg/kg of pentylenetetrazole (6,7,8,9-tetrahydro-5H-tetrazolo[1,5-a]azepine). After administration of the convulsive agent the animals were observed for 30 minutes. An animal was considered to be protected when the tonic extensor seizure was abolished on effect of the treatment with the test compound. The control group was treated with a placebo.

3) Measurement of the analgesic effect on mice

One hour after an oral pretreatment with various doses of the test compounds groups consisting of 10 mice each were intraperitoneally treated with 0.3 ml of a 0.6% by volume acetic acid solution as pain stimulus. The frequency of the writhing syndrome was recorded during a period of 30 minutes. The decrease caused by the treatment was related to the mean value of the writhing frequency observed in the control group. The $ED_{50}$ value was calculated from these differences expressed as percentages.

The results are summarized in the Table following hereinafter. The $ED_{50}$ values were calculated by using the probit analysis with 95% confidence limits.

The abbreviations used in the Table are as follows:
A: 1-[3,3-bis(4-fluorophenyl)-2-propenyl]-4-ethynyl-4-hydroxypiperidine hydrochloride
B: 1-[4,4-bis(4-fluorophenyl)-3-butenyl]-4-ethynyl-4-hydroxypiperidine hydrochloride
Imipramine: 5-(3-dimethylaminopropyl)-10,11-dihydro-5H-dibenzo[b,f]azepine
Nomifensine: 8-amino-2-methyl-4-phenyl-1,2,3,4-tetrahydroisoquinoline
NE: inactive in an oral dose of 30 mg/kg
p.o.: oral administration

TABLE

| | $ED_{50}$ p.o. (m/kg) | | |
|---|---|---|---|
| Compound | Inhibition of the tetrabenazine catalepsy | Inhibition of the pentylenetetrazole seizure | Inhibition of writhing syndrome |
| A | 30.0 | 30.0 | 30.0 |
| B | 18.7 | 21.0 | 13.7 |
| Imipramine | 25.1 | 35.4 | 30.0 |
| Nomifensine | 23.9 | NE | NE |

The new compounds of the formula (I) according to the invention possess an antidepressive effect which is equal to or higher than that of imipramine or nomifensine used as reference drugs. Their anticataleptogenic action is accompanied by a significant anticonvulsive effect; in addition as opposed to imipramine, no proconvulsive effect was observed on increasing the does of the compounds according to the invention.

The compounds according to the invention possess a pronounced analgesic effect being very advantageous in the treatment of psychotic disorders, e.g. reactive depression which can be developed on effect of pain sensation. Contrarily to imipramine, a further advantage appears therein that the compounds of the invention show no anticholinergic effect, which suggests a decrease in or elimination of side effects in the clinical practice in comparison to the reference drug. Due to their psychotropic, analgesic and anticonvulsive effects, the compounds of the formula (I) are useful for the systemic treatment of warm-blooded animals (including man). Here the term "systemic treatment" means oral, rectal or parenteral administration. The compounds of formula (I) can therapeutically be utilized for the treatment of e.g. psychotic disorders such as insomnia, mania, agitation, depression, anxiety, emesis, pains and dementia. The daily dosis depends on the severity of the disease and the status of the patient and amounts to 0.1-40 mg/kg which can be administered once or in several subdoses in oral, rectal or parenteral route.

The compounds according to the invention can be converted into pharmaceutical compositions. These compositions may be administered orally, rectally and/or parenterally. For oral administration, the composition may be formulated e.g. as a tablet, dragee or capsule. In order to prepare oral compositions, e.g. lactose or starch may be used as carriers. Gelatine, carboxymethylcellulose sodium, methylcellulose, polyvinylpyrrolidone or starch gum are suitable binding or granulation agents. As disintegrating agents mainly potato starch or microcrystalline cellulose may be added though ultraamylopectin or formaldehyde-casein and the like are also useful. Talc, colloidal silicic acid, stearin, calcium or magnesium stearate and the like are suitable anti-adhesive and sliding agents. Liquid oral compositions can be formulated e.g. as suspensions, syrups, or elixirs, which may contain water, glycols, oils, alcohols as well as coloring and flavoring agents.

Tablets may be prepared e.g. by compression following wet granulation. The mixture of the active ingredient with the carriers and optionally with a part of the disintegrating additive is granulated with an aqueous, alcoholic or aqueous-alcoholic solution of the binding agents in a suitable apparatus, then the granulate is dried. Subsequently, after mixing the other disintegrating, sliding and anti-adhesive additives to the dried granulate, the mixture is compressed to tablets. If desired, the tablets may be provided with a groove in order to facilitate the administration. Tablets may also directed by prepared from a mixture containing the active ingredient and suitable additives. The tablets may optionally be converted to dragees by employing commonly used pharmaceutical additives, e.g. protective, flavoring or coloring agents such as sugar, cellulose derivatives (methyl- or ethylcellulose, carboxymethylcellulose sodium and the like), polyvinylpyrrolidone, calcium phosphate, calcium carbonate, food dyes, dyeing lacquers, aromatizing agents, iron oxide, pigments and the like. Encapsulated compositions are prepared by filling a mixture of the active ingredient with the additives into capsules.

For rectal administration, the composition of the invention is formulated as a suppository containing a carrier mass, the so-called "adeps pro suppositorio" in addition to the active ingredient. As carriers, vegetable fats such as hardened vegetable oils, or triglycerides of $C_{12-18}$ fatty acids (preferably the carriers bearing the trade name Witepsol) may be used. The active ingredient is uniformly distributed in the molten carrier mass, then suppositories are prepared by moulding.

For parenteral administration, the composition of the invention is formulated as an injectable solution. For preparing these injectable solutions, the active ingredients are dissolved in distilled water and/or various organic solvents, e.g. glycol ethers, if desired, in the presence of solubilizing agents such as polyoxyethylene sorbitan monolaurate or monooleate or monostearate (Tween 20, Tween 60, or Tween 80), respectively. The injectable solution may further contain various auxiliary agents, e.g. preservatives such as ethylenediamine teraacetate as well as pH-modifying and buffering substances or, if desired, a local anaesthetic agent such as lidocaine. Before filling into the ampoules, the injectible solution containing the composition of the invention is filtered and after filling in, it is subjected to sterilization.

The invention also relates to a method for treating psychotic (psychiatric) disorders, insomnia, mania, agitation, depression, anxiety, emesis, dementia and pain. This method comprises administering a therapeutically effective amount of an active ingredient of the formula (I) or a pharmaceutically acceptable acid addition salt or quaternary ammonium salt thereof to the patient.

The invention is illustrated in detail by the aid of the following non-limiting Examples.

EXAMPLE 1

Preparation of 1-[4,4-bis(4-fluorophenyl)-3-butenyl]-4-ethynyl-4-hydroxypiperidine After introducing acetylene to a solution containing 19.2 g of potassium tert-butoxide in 125 ml of tetrahydrofuran at a temperature between 0° C. and −5° C. while stirring for 30 minutes, 39.0 g of 1-[4,4-bis(4-fluorophenyl)-3-butenyl]-piperidone dissolved in 90 ml of tetrahydrofuran are dropwise added and acetylene is introduced for one additional hour. Then the reaction mixture is cooled down to −10° C., aqueous saturated ammonium chloride solution is added under nitrogen, the tetrahydrofuran is evaporated under reduced pressure and the distillation residue is extracted with benzene. After washing the benzene layer with water and drying over anhydrous magnesium sulfate, the solution is evaporated under reduced pressure. After recrystallizing the residue from ethanol the title product is obtained in 92.8% yield, m.p.: 166–117° C.

The hydrochloride of the title free base melts at 210°–212° C.

Analysis of the free base: Calculated for $C_{23}H_{23}F_2NO$: C 75.18; H 6.31; F 10.34; N 3.81%; found: C 75.24; H 6.20; F 10.11; N 4.02%;

By using the appropriate starting substances the following compounds are prepared in an analogous manner as described in the preceding Example:

1-[3,3-bis(4-fluorophenyl)-2-propenyl]-4-ethynyl-4-hydroxypiperidine, m.p.: 138°–139° C.; hydrochloride m.p.: 189°–190° C.;

1-[3-(3-trifluoromethylphenyl)-3-(4-acetyloxyphenyl)-2-propenyl]-4-ethynyl-4-hydroxypiperidine hydrochloride, m.p.: 189°–190° C.;

1-[3,3-bis(3,5-dichlorophenyl)-2-propenyl]-4-ethynyl-4-hydroxoypiperidine oxalate, m.p.: 153°–155° C.; and 1-[4,4-bis(4-chlorophenyl)-3-butenyl]-4-ethynyl-4-hydroxypiperidine hydrochloride, m.p.: 217°–219° C.;

EXAMPLE 2

Preparation of 1-[4,4-bis(4-fluorophenyl)-3-butenyl]-4-acetyl-4-hydroxypiperidine hydrochloride 10.3 g of 9-[4,4-bis(4-fluorophenyl)-3-butenyl]-4-methylene-2-oxo-1,3-dioxa-8-azaspiro[4,5]decane are stirred with 100 ml of 2.8 mol/liter sodium hydroxide solution at 80°–90° C. under argon for 2 hours. After cooling down the reaction mixture is extracted with benzene and after washing the benzene phase with water to neutral and drying over anhydrous sodium sulfate, the solvent is evaporated under reduced pressure. The evaporation residue is dissolved in diisopropyl ether and the hydrochloride according to the title is precipitated by adding hydrogen chloride dissolved in diisopropyl ether to give the title hydrochloride in 91.3% yield, m.p.: 194°–198° C.

Analysis of the free base: Calculated for $C_{23}H_{23}F_2NO_2$: C 71.67; H 6.54; F 9.86; N 3.63%; found: C 71.71; H 6.32; F 10.01; N 3.66%.

EXAMPLE 3

Preparation of 1-(3,3-diphenyl-2-propenyl)-4-ethynyl-4-hydroxypiperidine

A solution of 16.5 g of 3,3-diphenyl-2-propenyl bromide in 70 ml of acetone is added dropwise to a mixture of 7.5 g of 4-ethynyl-4-hydroxypiperidine, 8.5 g of anhydrous potassium carbonate and 75 ml of anhydrous acetone at room temperature over 45 minutes, then the reaction mixture is stirred at room temperature for one hour. After filtering off the inorganic salts the solution is evaporated under reduced pressure. The residue is taken up in benzene, washed with water, dried over anhydrous sodium sulfate and the solution is evaporated under reduced pressure. After recrystallizing the residue from acetonitrile the title product is obtained in 68.4% yield, m.p.: 122°–123° C.

Analysis: Calculated for $C_{22}H_{23}NO$: C 83.24; H 7.30; N 4.41; found: C 83.27; H 7.44; N 4.57%.

The hydrochloride of the title base is precipitated from an ethereal solution of the base by adding ethereal hydrogen chloride solution, m.p.: 158°–161° C.

EXAMPLE 4

Preparation of 1-[4,4-bis(4-fluorophenyl)-3-butenyl]-4-butylcarbamoyloxy-4-ethynyl-piperidine A mixture containing 18.4 g of 1-[4,4-bis(4-fluorophenyl)-3-butenyl]-4-ethynyl-piperidine, 7.4 ml of butyl isocyanate and 90 ml of triethylamine is gently refluxed under nitrogen while stirring for 7 to 8 hours. After evaporating the reaction mixture under reduced pressure, the residue is taken up in methanol, the solution is clarified by activated carbon at room temperature, then the methanol is distilled off under reduced pressure. After recrystallization of the crude product from a mixture of diisopropyl ether and hexane the title product is obtained in 82.2% yield, m.p.: 83°–84° C.

Analysis: Calculated for $C_{28}H_{32}F_2N_2O_2$: C 72.08; H 6.91; F 8.14; N 6.00%; found: C 72.221 H 7.13; F 8.11; N 6.17%.

By using the appropriate starting substances the following compounds are prepared in an analogous manner as described in the preceding Example:

4-acetyl-1-[4,4-bis(4-fluorophenyl)-3-butenyl]-4-phenylcarbamoyloxypiperidine, m.p.: 139°–141° C.

4-cyclohexylcarbamoyloxy-1-(3,3-diphenyl-2-propenyl)-4-ethynylpiperidine hydrochloride, m.p.: 237°–240° C. (with decomposition);

4-acetyl-1-(3,3-diphenyl-2-propenyl)-4-ethylcarbamoyloxypiperidine hydrochloride, m.p.: 190°–192° C.; and 1-[4,4-bis(1-chlorophenyl)-3-butenyl]-4-[4-chlorophenyl)-carbamoyloxy]-4-ethynyl-piperidine hydrochloride hydrochloride, m.p.: 244°–247° C. (with decomposition).

EXAMPLE 5

Preparation of 4-benzylcarbamoyloxy-1-[4,4-bis(4-fluorophenyl)-3-butenyl]-4-ethynyl-piperidine 9.8 g of 1-[4,4-bis(4-fluorophenyl)-3-butenyl]-4-ethynyl -4-phenoxycarbonyloxypiperidine are stirred with 9 ml of benzylamine at 42° C. under nitrogen for 30 minutes, then at room temperature for 10 hours. Thereafter, benzene is added to the reaction mixture and washed first with an aqueous sodium hydroxide solution of 1 ml/liter concentration, then with water and dried over anhydrous magnesium sulfate. After evaporating the solution under reduced pressure, the residue is boiled in hexane and after filtration it is recrystallization from diisopropyl ether to give the title product in 75.7% yield, m.p.: 94°–95° C.

Analysis: Calculated for $C_{31}H_{30}F_2N_2O_2$: C 74.38; H 6.04; F 7.59; N 5.60%; found: C 74.22; H 5.69; F 7.69; N 5.53%.

By using the appropriate starting substances the following compounds are prepared in an analogous manner as described in the preceding Example:

1-[4,4-bis(4-fluorophenyl)-3-butenyl]-4-[[2-(3,4-dimethoxyphenyl)ethyl]carbamoyloxy]-4-ethynyl-piperidine maleate, m.p.: 53°–54° C.

1-[4,4-bis(4-fluorophenyl)-3-butenyl]-4-carbamoyloxy-4-ethynylpiperidine hydrochloride, m.p.: 206°–207° C.

EXAMPLE 6

Preparation of 4-acetyl-1-[3,3-bis(4-fluorophenyl)-2-propenyl]-4-hydroxypiperidine hydrochloride After dissolving 10.6 g of 1-[3,3-bis(4-fluorophenyl)-2-propenyl]-4-ethynyl-4-hydroxypiperidine in the mixture of 37.5 ml of acetic acid and 1.5 ml of acetic anhydride at 25° C., 10.5 g of mercuric acetate are added in four portions. After stirring for 7 hours the reaction mixture is left to stand overnight, then gaseous hydrogen sulfide is introduced for one hour under stirring. After standing for 3 hours the precipitate is filtered, washed with acetic acid and the solution is evaporated under reduced pressure. The residue is taken up in ether, washed with aqueous sodium carbonate solution of 10% by weight and then with water, dried over anhydrous magnesium sulfate and evaporated under reduced pressure. After adding methanolic potassium hydroxide solution of 5% by weight, the residue is stirred under nitrogen at room temperature for one hour, then diluted with water and extracted with benzene. The benzene phase is washed to neutral, dried over anhydrous sodium sulfate and evaporated under reduced pressure. The residue is transformed to the hydrochloride by adding hydrogen chloride dissolved in diisopropyl ether to obtain the title hydrochloride in 72.1% yield, m.p.: 257°–259° C.

Analysis: Calculated for $C_{22}H_{23}F_2NO_2$: C 71.14; H 6.24; F 10.23; N 3.77%; found: C 71.35 H 6.60; F 10.11; N 3.79%.

EXAMPLE 7

The new compounds according to the invention can be converted e.g. to the following pharmaceutical compositions.

a) Preparation of tablets 50.0 g of active ingredient are mixed together with 92 g of lactose, 40 g of potato starch, 4 g of polyvinylpyrrolidine, 6 g of talc, 1 g of magnesium stearate, 1 g of colloidal silicon dioxide (Aerosil) and 6 g of ultraamylopectin and, after wet granulation, the product obtained is compressed to tablets containing 50 mg of the active ingredient each.

b) Preparation of dragees

After coating the tablets prepared as described above in a known manner with a layer consisting of sugar and talc, the dragees obtained are polished with a mixture of bee's wax and carnauba wax to obtain dragees weighing 250 mg each.

c) Preparation of capsules 100 g of active ingredient are thoroughly mixed together with 30 g of sodium lauryl sulfate, 280 g of starch, 280 g of lactose, 4 g of colloidal silicon dioxide (Aerosil) and 6 g of magnesium stearate, then the mixture is sieved and filled into hard gelatine capsules to obtain capsules containing 100 mg of active ingredient each.

d) Preparation of suppositories 100.0 mg of active ingredient are thoroughly mixed together with 200.0 mg of lactose; 1700.0 mg of suppository base (e.g. Witepsol 4)(all calculated for one suppository) are molten, cooled to 35° C. and the mixture of the active ingredient and lactose is mixed thereto by using a homogenizer. The product obtained is poured into cooled conical molds. Each suppository weighs 2000 mg.

e) Preparation of a suspension

| Components in 100 ml of the suspension: | |
| --- | --- |
| Active ingredient | 1.00 g |
| Sodium hydoxide | 0.26 g |
| Citric acid | 0.30 g |
| Nipagin (methyl 4-hyroxybenzoate sodium salt) | 0.10 g |
| Carbapol 940 polyacrylic acid | 0.30 g |
| 96% Ethanol | 1.00 g |
| Raspberry flavor | 0.60 g |
| Sorbitol (Aqueous solution of 70%) | 71.00 g |
| Distilled water up to | 100.00 ml |

After adding Carbopol in little portions to the solution of Nipagin and citric acid in 20 ml of distilled water under vigorous stirring, the solution obtained is allowed to stand for 10 to 12 hours. Subsequently, the amount given above of sodium hydroxide dissolved in 1 ml of destilled water, the aqueous solution of sorbitol and finally the ethanolic solution of the raspberry flavor are dropped in under stirring. The active ingredient is added in small portions to this mixture and suspended by using a submerged homogenizer. Finally, the suspension is supplemented to 100 ml by adding distilled water and the syrupy suspension is led through a colloid mill.

We claim:

1. A compound of the formula (1)

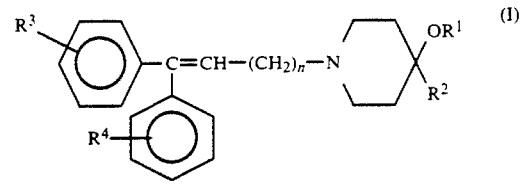

wherein $R^1$ means hydrogen or —CONHR group, wherein

R stands for hydrogen, $C_{1-12}$alkyl, $C_{3-6}$cycloalkyl, carbocyclic $C_{6-10}$aryl or carbocyclic $C_{6-10}$aryl-$C_{1-4}$alkyl group, the latter two being unsubstituted or substituted on their aromatic moiety by at least one same or different halogen, $C_{1-4}$alkyl or $C_{1-4}$alkoxy group;

$R^2$ stands for an ethynyl or acetyl group;

$R^3$ and $R^4$, which are the same or different, represent hydrogen, or at least one halogen, $C_{1-4}$alkyl, $C_{1-4}$alkoxy, trihalomethyl group or hydroxyl group free or esterified by a $C_{1-4}$alkanoic acid; and n is 1 or 2,
or a pharmaceutically acceptable acid addition or quaternary ammonium salts thereof.

2. The compound of the Formula (I) defined in claim 1 wherein n is 2, or a pharmaceutically acceptable acid addition of quaternary ammonium salt thereof.

3. A compound as defined in claim 1 and selected from the group consisting of
1-[3,3-bis(4-fluorophenyl)-2-propenyl]-4-ethynyl-4-hydroxypiperidine or its hydrochloride,
1-[4,4-bis(4-fluorophenyl)-3-butenyl]-4-ethynyl-4-hydroxy-piperidine or its hydrochloride, and
1-[4,4-bis(4-fluorophenyl)-3-butenyl]-4-benzylcarbamoyloxy-4-ethynylpiperidine
or a pharmaceutically acceptable acid addition or quaternary ammonium salt of these compounds.

4. A pharmaceutical composition for treating depression, which comprises as active ingredient an anti-depressantly effective amount of the compound of the Formula (I) as defined in claim 1, or a pharmaceutically acceptable acid addition or quaternary ammonium salt thereof.

5. A method for the treatment of depression in a mammalian subject which comprises the step of administering to said mammal to be treated an anti-depressantly effective amount of the compound of the Formula (I) as defined in claim 1, or a pharmaceutically acceptable acid addition or quaternary ammonium salt thereof alone or in the form of a pharmaceutical composition.

6. 1-{3,3-bis(4-fluorophenyl)-2-propenyl}-4-ethynyl-4-hydroxypiperidine as defined in claim 1 or a pharmaceutically acceptable acid addition or quaternary ammonium salt thereof as defined in claim 1.

7. 1-{4,4-bis(4-fluorophenyl)-3-butenyl}-4-ethynyl-4-hydroxypiperidine as defined in claim 1 or a pharmaceutically acceptable acid addition or quaternary ammonium salt thereof as defined in claim 1.

* * * * *